(12) United States Patent
Yan et al.

(10) Patent No.: US 12,350,519 B2
(45) Date of Patent: Jul. 8, 2025

(54) POSITIONING METHOD, PROCESSING DEVICE, RADIOTHERAPY SYSTEM, AND STORAGE MEDIUM

(71) Applicant: OUR UNITED CORPORATION, Xi'an (CN)

(72) Inventors: Hao Yan, Xi'an (CN); Tianchang Gou, Xi'an (CN); Jinsheng Li, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 488 days.

(21) Appl. No.: 17/935,310

(22) Filed: Sep. 26, 2022

(65) Prior Publication Data

US 2023/0102782 A1  Mar. 30, 2023

(30) Foreign Application Priority Data

Sep. 26, 2021 (CN) .......................... 202111131773.X (51) Int. Cl.
*A61N 5/00* (2006.01)
*A61N 5/10* (2006.01)

(52) U.S. Cl.
CPC .... *A61N 5/1049* (2013.01); *A61N 2005/1059* (2013.01)

(58) Field of Classification Search
CPC .................. A61N 5/1049; A61N 2005/1059
USPC ........................................ 250/492.1–492.3
See application file for complete search history.

(56) References Cited

U.S. PATENT DOCUMENTS

2024/0001151 A1* 1/2024 Sabel .................. G06T 7/0014

* cited by examiner

*Primary Examiner* — Michael Maskell
(74) *Attorney, Agent, or Firm* — Kolitch Romano Dascenzo Gates LLC (57) ABSTRACT

The present disclosure discloses a positioning method, a processing device, a radiotherapy system and a storage medium, which belong to the field of medical technologies. The method includes: acquiring a three-dimensional body surface image of a patient on a support apparatus after receiving a positioning instruction; determining a first deviation between the three-dimensional body surface image of the patient and a first body surface reference image in each coordinate direction in the three-dimensional coordinate system, based on the three-dimensional body surface image of the patient and the first body surface reference image, so that the support apparatus is movable according to the first deviations in the various coordinate directions until the first deviations are within a preset threshold range after the movement.

20 Claims, 5 Drawing Sheets

POSITIONING METHOD, PROCESSING DEVICE, RADIOTHERAPY SYSTEM, AND STORAGE MEDIUM

The present disclosure claims priority to Chinese Patent Application No. 202111131773.X, filed on Sep. 26, 2021 and entitled "POSITIONING METHOD, PROCESSING DEVICE, RADIOTHERAPY SYSTEM, AND STORAGE MEDIUM", the entire contents of which are incorporated herein by reference.

TECHNICAL FIELD

The present disclosure relates to the field of medical technologies, and in particular to a positioning method, a processing device, a radiotherapy system and a storage medium.

BACKGROUND

Radiotherapy is an important means of treating cancer, and a radiotherapy device is a key medical device for radiotherapy. Currently, before a patient is treated with a radiotherapy device, the patient on a support apparatus (for example, a treatment couch) of the radiotherapy device needs to be positioned (also called as setup), so that a target point (for example, a target in gamma-knife treatment) of the patient's part to be treated coincides with an isocenter of the radiotherapy device.

SUMMARY

Embodiments of the present disclosure provide a positioning method, a processing device, a radiotherapy system, and a storage medium. It can solve the problems of low accuracy and efficiency of positioning the patient using the laser light at present. The technical solutions are as follows.

In one aspect, a positioning method is provided. The method includes:
acquiring a three-dimensional body surface image of a patient on a support apparatus after receiving a positioning instruction;
determining a first deviation between the three-dimensional body surface image of the patient and a first body surface reference image in each coordinate direction in the three-dimensional coordinate system, based on the three-dimensional body surface image of the patient and the first body surface reference image so that the support apparatus is movable according to the first deviation in each coordinate direction until the first deviation is within a preset threshold range after movement.

Optionally, the first deviation in each coordinate direction includes a translation offset in each coordinate direction, the preset threshold range includes a preset translation offset threshold range.

Optionally, the first deviation in each coordinate direction further includes a rotation offset in each coordinate direction, the preset threshold range further includes a preset rotation offset threshold range.

Optionally, in a case that the support apparatus is a three-dimensional couch, the method further includes:
detecting whether the rotation offsets in various coordinate directions are within the preset rotation offset threshold range;
outputting first prompt information in response to detecting that a rotation offset in at least one coordinate direction of the rotation offsets in various coordinate directions is not within the preset rotation offset threshold range, the first prompt information used for prompting an operator to adjust a position of the patient on the support apparatus.

Optionally, the method further includes:
determining the translation offset in each coordinate direction as a correction offset response to detecting that the rotation offsets in the various coordinate directions are within the preset rotation offset threshold range so that the support apparatus is movable according to the correction offset until the first deviation is within the preset translation offset threshold range after movement.

Optionally, the method further includes:
detecting whether the translation offset in each coordinate direction is within the preset translation offset threshold range;
outputting second prompt information according to a detection result, the second prompt information used to prompt the operator that the translation offset in at least one coordinate direction of the translation offsets in various coordinate directions is outside the preset translation offset threshold range.

Optionally, the method further includes:
re-performing an operation of acquiring the three-dimensional body surface image of the patient in response to receiving the positioning instruction again.

Optionally, the method further includes:
outputting a first deviation in each coordinate direction.

Optionally, the method further includes:
acquiring another three-dimensional body surface image of the patient on the support apparatus after receiving an instruction for monitoring a movement of the patient during treatment;
determining a second deviation between the three-dimensional body surface image of the patient and a second body surface reference image in each coordinate direction, based on the three-dimensional body surface image of the patient and the second body surface reference image, to monitor the movement of the patient.

Optionally, the second body surface reference image is a three-dimensional image of the body surface of the patient on the support apparatus after a first deviation in various coordinate directions is within the preset threshold range.

Optionally, the second body surface reference image is the first body surface reference image.

Optionally, acquiring the three-dimensional body surface image of the patient includes:
acquiring the three-dimensional body surface image of the patient by a stereo camera.

Optionally, the method further includes:
overlaying at least two of the three-dimensional body surface image of the patient, the first body surface reference image, and a real-time image of the patient.

Optionally, the method further includes:
acquiring a plurality of medical pictures of a patient;
generating the first body surface reference image based on outer contours of the patient in the plurality of medical pictures.

In another aspect, a processing device is provided. The processing device includes a processor, and a memory for storing executable instructions of the processor, and the processor is configured to perform the positioning method described above.

In yet another aspect, a radiotherapy system is provided. The radiotherapy system includes a processing device and a radiotherapy device, the radiotherapy device includes a support apparatus, and the processing device is the processing device described above.

Optionally, the radiotherapy system further includes a trigger apparatus which connects and communicates with the processing device, and the trigger apparatus is configured to send a positioning instruction to the processing device.

Optionally, the radiotherapy system further includes a display which connects and communicates with the processing device, the display is configured for displaying an overlaid image of at least two of the three-dimensional body surface image of the patient, the first body surface reference image and the real-time image of the patient.

Optionally, the radiotherapy system further includes a photographing apparatus which connects and communicates with the processing device, and the photographing apparatus is configured to photograph a real-time image of the patient.

In still another aspect, a non-transitory computer-readable storage medium is provided. Instructions are stored in the non-transitory computer-readable storage medium, and when the non-transitory computer-readable storage medium runs on a processing assembly, the processing assembly executes the positioning method described above.

The beneficial effects brought by the technical solutions according to the embodiments of the present disclosure include at least:

after receiving a positioning instruction, the support apparatus is controlled to move, by acquiring a body surface image of the patient and based on the three-dimensional body surface image of the patient and a first body surface reference image. After deviation between the three-dimensional body surface image of the patient and the first body surface reference image in various coordinate directions in the three-dimensional coordinate system is within a preset threshold range, the target point of the patient on the patient support apparatus coincides with the isocenter of the radiotherapy device, to complete the positioning of the patient. In this way, as long as the positioning instruction is received, the patient can be positioned automatically by the body surface image. The patient can be positioned without manual adjustment by the operator, which completely replaces the laser light and improves the accuracy and efficiency of positioning the patient.

BRIEF DESCRIPTION OF THE DRAWINGS

For clearer descriptions of the technical solutions in the embodiments of the present disclosure, the following briefly introduces the accompanying drawings required for describing the embodiments. Apparently, the accompanying drawings in the following description show merely some embodiments of the present disclosure, and persons of ordinary skill in the art may still derive other drawings from these accompanying drawings without creative efforts.

DETAILED DESCRIPTION

For clearer descriptions of the objectives, technical solutions, and advantages of the present disclosure, embodiments of the present disclosure are described in detail hereinafter with reference to the accompanying drawings.

In the related art, a laser light in the radiotherapy device is usually used to position a patient. For example, the laser light can emit three intersecting laser beams toward different directions. When positioning the patient, the treatment couch can be moved so that three cross markers on the patient's body surface coincide with the cross laser rays of the three laser beams respectively, and thus the target of the patient can coincide with the isocenter of the radiotherapy device.

However, when the laser light is used to position the patient, the operator needs to manually control the buttons on the operation panel of the radiotherapy device according to the laser beams of the laser light to adjust the treatment couch. The positioning accuracy and efficiency are low.

Figure 1:
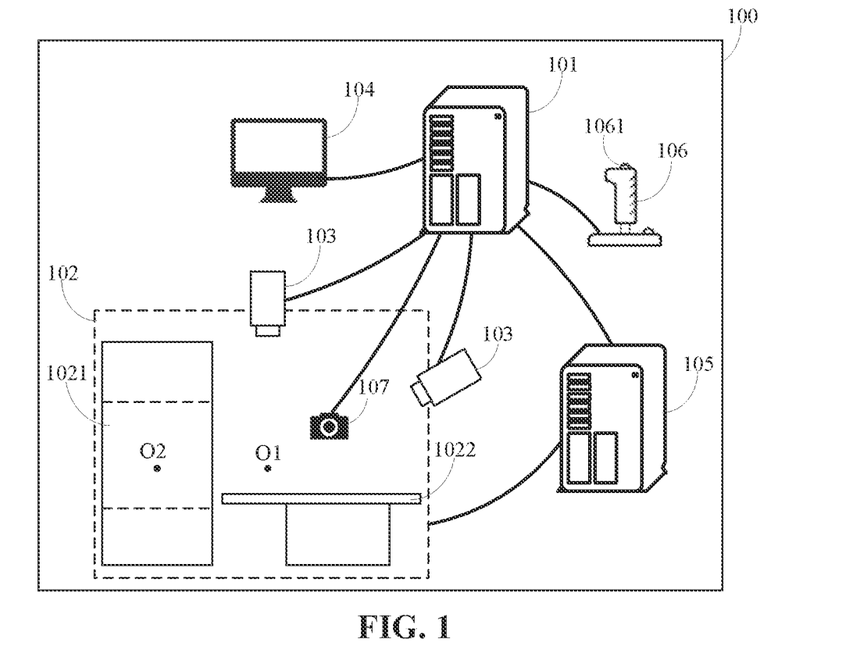
FIG. 1 is a schematic structural diagram of a radiotherapy system involved in a positioning method according to an embodiment of the present disclosure.
Figure 2:
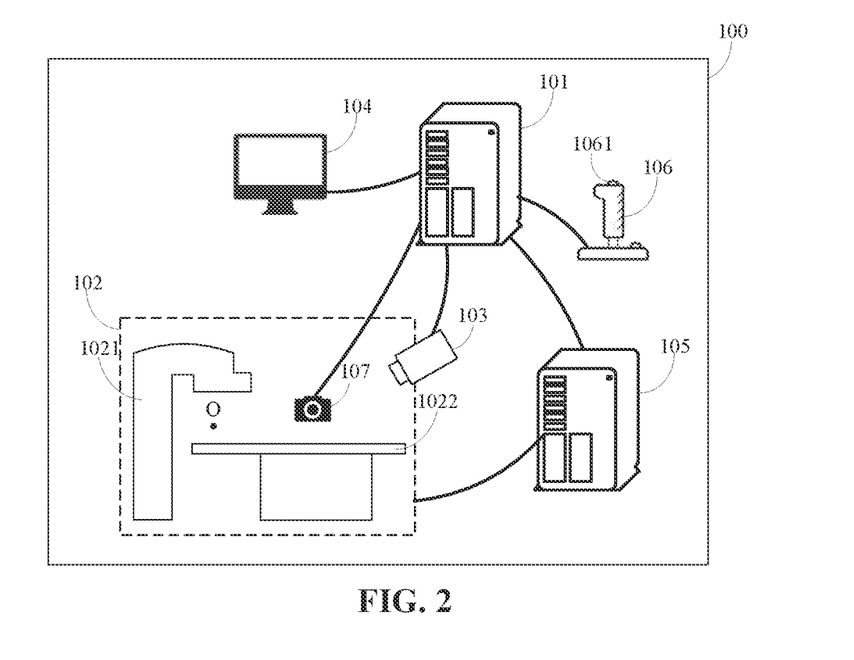
FIG. 2 is a schematic structural diagram of a radiotherapy system involved in another positioning method according to an embodiment of the present disclosure.

Referring to FIG. 1 and FIG. 2, FIG. 1 is a schematic structural diagram of a radiotherapy system involved in a positioning method according to an embodiment of the present disclosure, and FIG. 2 is a schematic structural diagram of a radiotherapy system involved in another positioning method according to an embodiment of the present disclosure. The radiotherapy system 100 may include a processing device 101 and a radiotherapy device 102.

The processing device 101 may be a server, or a server cluster composed of several servers, or a cloud computing service center, or the like.

The radiotherapy device 102 may be a gamma knife or a medical electron linear accelerator or the like. The radiotherapy device 102 may include a rotating gantry 1021 carrying a radiation head, and a support apparatus 1022. The support apparatus 1022 may generally be a treatment couch.

Optionally, the radiotherapy system 100 may further include a stereo camera 103. The stereo camera 103 may be a structured light camera, and the stereo camera 103 may face the support apparatus 1022 in the radiotherapy device 102. In this way, after the patient is on the support apparatus 1022, the stereo camera 103 may emit structured light to the patient on the support apparatus 1022, and receive the structured light reflected by the body surface of the patient, so that the stereo camera 103 can acquire a three-dimensional body surface image of the patient.

In the embodiments of the present disclosure, the stereo camera 103 may connect and communicate with the processing device 101. After the stereo camera 103 acquires the three-dimensional body surface image of the patient, it may also send the three-dimensional body surface image of the patient to the processing device 101.

Optionally, the radiotherapy system 100 may further include a display 104 which connects and communicates with the processing device 101. After the processing device 101 receives the three-dimensional body surface image of the patient, the processing device 101 may display the three-dimensional body surface image of the patient on the display 104.

Optionally, the radiotherapy system 100 may further include a control device 105 which connects and communicates with the processing device 101. The control device 105 may be a computer for sending a control command. For example, the control device 105 may be a computer device such as a server. After the processing device 101 receives the three-dimensional body surface image of the patient, the processing device 101 may send a first deviation between the three-dimensional body surface image of the patient and a first body surface reference image to the control device 105 according to the relative position between the three-dimensional body surface image of the patient and the first body surface reference image. After receiving the first deviation, the control setting 105 may control the movement of the support apparatus 1022 based on the first deviation in order to complete the process of positioning the patient.

In an example, the processing device 101 may be a host computer, and the control device 105 may be a slave computer. The host computer may connect and communicate with the slave computer, and after the host computer sends a control command to the slave computer, the slave computer may control a movement control assembly (such as a driver) of the support apparatus 1022 to drive the support apparatus 1022 to move.

It should be noted that, in other possible implementations, the processing device 101, the display 104 and the control device 105 in the above embodiments may be integrated in the same physical machine; or the display 104 and the processing device 101 in the above embodiments may be integrated in the same physical machine; or the processing device 101 and the control device 105 in the above embodiments may be integrated in the same physical machine. When the processing device 101 and the display 104 are integrated in the same physical machine, the processing device 101 is the host computer.

Optionally, as shown in FIG. 1 and FIG. 2, the radiotherapy system 100 may further include a trigger apparatus 106. The trigger apparatus 106 may connect and communicate with the processing device 101, and the trigger apparatus 106 is used for sending a positioning instruction to the processing device 101 so that the processing device 101 can acquire the three-dimensional body surface image of the patient on the support apparatus 1022 through the stereo camera 103. In an example, the trigger apparatus 106 may be a handle with a button 1061. The operator may hold the trigger apparatus 106, and after the button 1061 is pressed, the processing device 101 may receive the positioning instruction triggered by the operator.

It should be noted that, in other optional implementations, the trigger apparatus 106 may be a virtual key, which may be displayed on the display 104 in the above embodiments. In this case, the display interface of the display 104 may display a first virtual key of "one-key positioning". After the operator presses the first virtual key, the processing device 101 may receive the positioning instruction triggered by the operator. It should also be noted that, in the following embodiments, that the trigger apparatus 106 displayed on the display 104 is taken as an example, so as to schematically illustrate how the processing device 101 receives the positioning instruction triggered by the operator.

Optionally, as shown in FIG. 1 and FIG. 2, the radiotherapy system 100 may further include a photographing apparatus 107. The photographing apparatus 107 may be an optical video camera, and may face the support apparatus 1022 in the radiotherapy device 102. In this way, after the patient is on the support apparatus 1022, a real-time image of the patient on the support apparatus 1022 may be captured by the photographing apparatus 107. In the present disclosure, the photographing apparatus 107 may connect and communicate with the processing device 101, and after the photographing apparatus 107 captures the real-time image of the patient, it may also send the real-time image of the patient to the processing device 101. In this way, after the processing device 101 receives the real-time image of the patient, it may overlay at least two images of the real-time image, the three-dimensional body surface image and the first body surface reference image of the patient, and send the overlaid image to the display 104, so that the display 104 can display the overlaid image of at least two of the real-time image of the patient, the three-dimensional body surface image, and the first body surface reference image.

In the embodiments of the present disclosure, according to different structures of the rotating gantry 1021 in the radiotherapy device 102, the radiotherapy device 102 may be classified into two types of radiotherapy devices, including a roller type radiotherapy device and a C-arm type radiotherapy device, respectively.

As shown in FIG. 1, in a case that the radiotherapy device 102 is a roller type radiotherapy device, the rotating gantry 1021 in the radiotherapy device 102 is a roller. The radiotherapy device 102 has two isocenters, including a virtual isocenter O1 and an actual isocenter O2, respectively. After the patient is on the support apparatus 1022, the patient on the support apparatus 1022 needs to be positioned so that the target point of the patient on the support apparatus 1022 coincides with the virtual isocenter O1 of the radiotherapy device 102. Then, after the patient support apparatus 1022 moves by a preset distance, the target point of the patient may coincide with the actual isocenter O2 of the radiotherapy device 102, so as to ensure that the radiotherapy device 102 can treat the patient. In this case, the number of stereo cameras 103 may be two. One stereo camera 103 may face the virtual isocenter O1 and is used to acquire a three-dimensional body surface image of the patient in the positioning (or setup) stage before treatment; and the other stereo camera 103 may face the actual isocenter O2 and is used to acquire a three-dimensional body surface image of the patient in the treatment stage.

As shown in FIG. 2, in a case that the radiotherapy device 102 is a C-arm type radiotherapy device, the rotating gantry 1021 in the radiotherapy device 102 is a C-arm. The radiotherapy device 102 has only one isocenter O. After the patient is on the support apparatus 1022, the patient on the support apparatus 1022 needs to be positioned so that the target point of the patient on the support apparatus 1022 coincides with the isocenter O of the radiotherapy device 102, which ensures that the radiotherapy device 102 can treat the patient. In this case, the number of the stereo camera 103 may be one, and the stereo camera 103 may acquire the three-dimensional body surface image of the patient in the positioning stage before treatment, and may also acquire the three-dimensional body surface image of the patient in the treatment stage.

Figure 3:
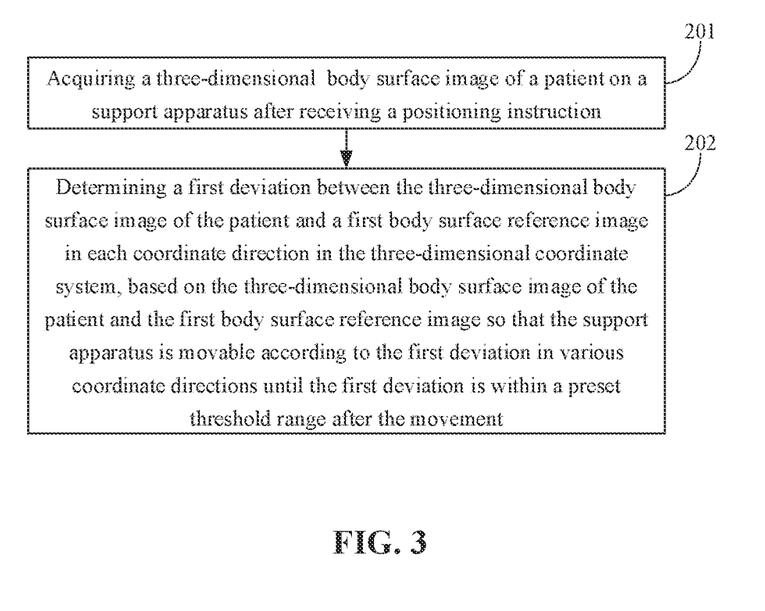
FIG. 3 is a flowchart of a positioning method according to an embodiment of the present disclosure.

Reference is made to FIG. 3, which is a flowchart of a positioning method according to an embodiment of the present disclosure. The positioning method is applicable to the processing device 101 in the radiotherapy system 100 shown in FIG. 1 or FIG. 2. The positioning method may include the following steps.

In step 201, a three-dimensional body surface image of a patient on a support apparatus is acquired after a positioning instruction is received.

In step 202, a first deviation between the three-dimensional body surface image of the patient and a first body surface reference image in each coordinate direction in the three-dimensional coordinate system is determined, based on the three-dimensional body surface image of the patient and the first body surface reference image, so that the support apparatus can move according to the first deviation in various coordinate directions until the first deviation is within a preset threshold range after the movement.

The patient's target point is the patient's target. The first body surface reference image is a three-dimensional contour image of the patient's body surface when the target point of the patient coincides with the isocenter of the radiotherapy device. The three-dimensional coordinate system may be the isocenter coordinate system of the radiotherapy device or the three-dimensional coordinate system of the support apparatus. It should be noted that the three-dimensional coordinate system being the three-dimensional coordinate system of the support apparatus is taken as an example for schematic illustration in the following embodiments.

In the embodiments of the present disclosure, the first body surface reference image is a pre-acquired image, which may be a three-dimensional contour image of the patient's body surface when the target point of the patient coincides with the isocenter of the radiotherapy device. In this way, after the processing device acquires the first body surface reference image of the patient, the processing device may determine the first deviation between the three-dimensional body surface image of the patient and the first body surface reference image based on the three-dimensional body surface image of the patient and the first body surface reference image, so that the support apparatus can move according to the first deviation. During the movement of the support apparatus, the first deviation between the three-dimensional body surface image of the patient and the first body surface reference image gradually decreases. After the first deviation is within the preset threshold range, the target point of the patient on the patient support apparatus coincides with the isocenter of the radiotherapy device, and the positioning of the patient is completed.

In summary, in the positioning method according to the embodiments of the present disclosure, the body surface image of the patient is acquired, and the first deviation between the three-dimensional body surface image of the patient and the first body surface reference image is determined based on the three-dimensional body surface image of the patient and the first body surface reference image, so that the support apparatus can move according to the first deviation. After the first deviation is within the preset threshold range, the target point of the patient on the patient support apparatus coincides with the isocenter of the radiotherapy device, and the positioning of the patient is completed. In this way, as long as the positioning instruction is received, the patient may be positioned automatically through the body surface image. The patient can be positioned without manual adjustment by the operator, which completely replaces the laser light and improves the accuracy and efficiency of positioning the patient.

Figure 4:
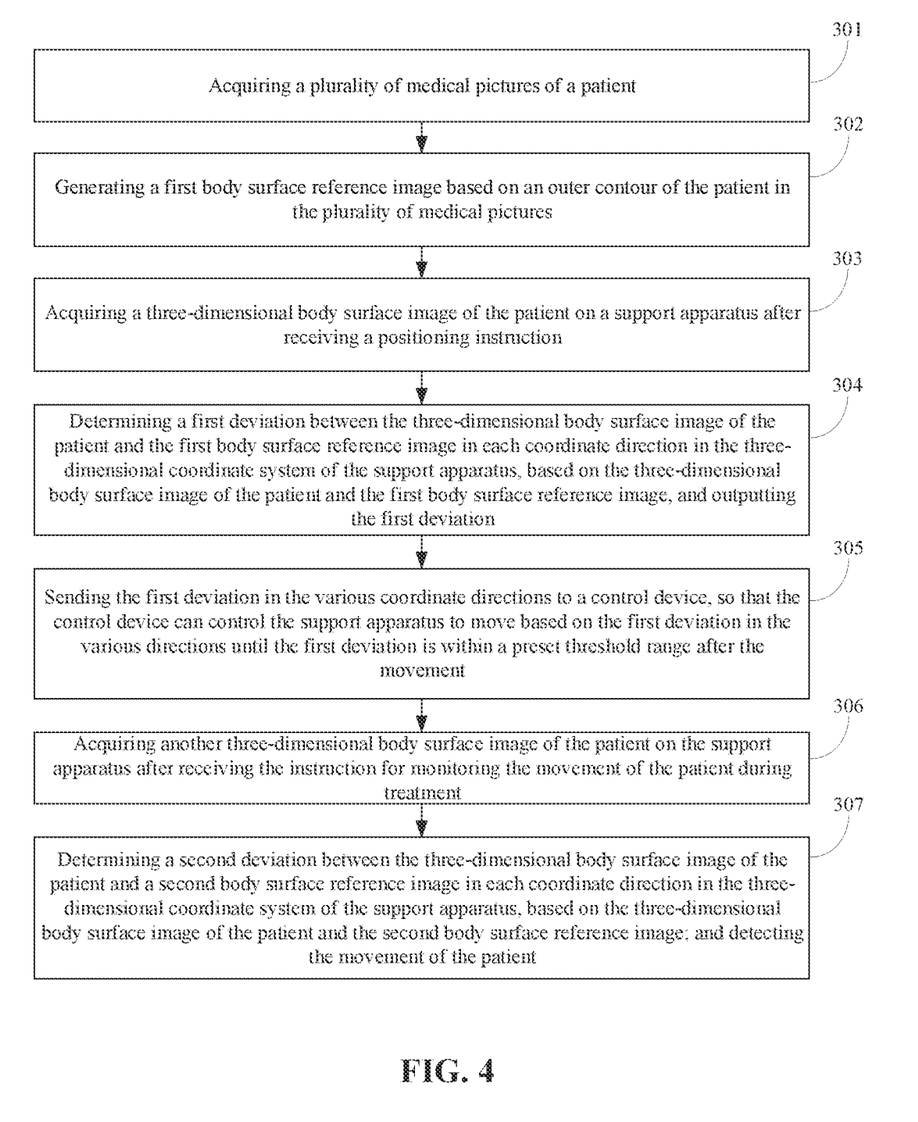
FIG. 4 is a flowchart of another positioning method according to an embodiment of the present disclosure.

Reference is made to FIG. 4, which is a flowchart of another positioning method according to an embodiment of the present disclosure. The positioning method is applicable to the processing device 101 in the radiotherapy system 100 shown in FIG. 1. The positioning method may include the following steps.

In step 301, a plurality of medical pictures of a patient are acquired.

In the embodiments of the present disclosure, the processing device may acquire a plurality of medical pictures of the patient.

In an example, before the patient is treated with the radiotherapy device, the doctor needs to develop a treatment plan for the patient. The treatment plan contains a plurality of medical pictures of the patient, and the treatment plan is stored in a radiation Treatment Planning System (TPS) server. To this end, that the plurality of medical pictures of the patient are acquired by the processing device includes that the processing device acquires the plurality of medical pictures of the patient from the TPS server. To this end, the processing device needs to connect and communicate with the TPS server to acquire the plurality of medical pictures of the patient stored in the TPS server.

It should be noted that, each medical picture is usually a picture acquired by photographing a patient with a medical imaging device. For example, the medical imaging device may be a Computed Tomography (CT) device or a Magnetic Resonance Imaging (MRI) device. The medical picture may include an outer contour of the patient (i.e., the contour of the patient's body surface), and a picture of the patient's tumor. When the doctor develops the treatment plan for the patient, the target point of the patient may be determined from the medical pictures according to the medical pictures. The patient's target point is the patient's target. To this end, the medical pictures stored in the treatment server contain the position information of the patient's target point.

In step 302, a first body surface reference image is generated, based on the outer contour of the patient in the plurality of medical pictures.

In the embodiments of the present disclosure, the medical pictures acquired by the processing device may include an outer contour of a patient. In this way, the processing device may generate the first body surface reference image based on the outer contour of the patient in the plurality of medical pictures.

In an example, each medical picture may be a section picture of a patient in a transverse plane, and the positions of the sections of the patient in the transverse plane in various medical pictures are different. The plurality of medical pictures may be arranged according to the positions of the sections of the patient in the transverse plane. The processing device may extract the outer contour of the patient in each of the plurality of medical pictures, and splices the extracted plurality of contours according to the arrangement order of the plurality of medical pictures to acquire the first body surface reference image.

It should be noted that, since the medical pictures are pictures acquired by photographing the patient with a medical imaging device, the coordinate information of the outer contour of the patient in the medical pictures is the coordinate information in the three-dimensional coordinate system of the medical imaging device. Therefore, the coordinate information of each data point or point cloud data in the first body surface reference image generated by the processing device based on the outer contour of the patient in the plurality of medical pictures is the coordinate information in the three-dimensional coordinate system of the medical imaging device. Therefore, the processing device also needs to convert the coordinate system of each data point or point cloud data in the first body surface reference image into the coordinate information in the three-dimensional coordinate system of the support apparatus according to the calibration relationship between the three-dimensional coordinate system of the medical imaging device and the three-dimensional coordinate system of the support apparatus.

Moreover, the medical pictures contain the position information of the target point of the patient. Therefore, after the processing device generates the first body surface reference image, the positional relationship between the target point of the patient and the first body surface reference image is also determined. In this way, in the three-dimensional coordinate system of the support apparatus, after the target point of the patient coincides with the isocenter of the radiotherapy device, the first body surface reference image may represent a three-dimensional contour image of the body surface of the patient when the target point of the patient coincides with the isocenter of the radiotherapy device.

In step 303, a three-dimensional body surface image of the patient on the support apparatus is acquired after the positioning instruction is received.

In the embodiments of the present disclosure, after the processing device receives the positioning instruction, the processing device may acquire a three-dimensional body surface image of the patient on the support apparatus.

In a possible implementation, the positioning instruction may be triggered by an operator. In an example, the display interface of the display which connects and communicates with the processing device may display the first virtual key of "one-key positioning". After the patient is on the support apparatus, the operator may press the first virtual key on the display interface of the display, so that the processing device may receive the positioning instruction triggered by the first virtual key, and thus the processing device may acquire the three-dimensional body surface image of the patient.

In another possible implementation, a human-computer interaction as described above, that is, the mode of triggering the positioning instruction, may be replaced by a computer pre-programming process, for example, a behavior mechanism or an operation mechanism of the operator is intelligentized according to simulation learning. In an example, the positioning instruction may also be automatically generated by the processing device after the support apparatus satisfies a specific triggering condition. The specific triggering condition may include: it is detected that the patient is on the support apparatus for the first time, or it is detected that the patient moves on the support apparatus and a predetermined delay time has elapsed. For example, a detection assembly (e.g., a human sensor and/or a gravity sensor, etc.) for detecting the patient may be provided on the support apparatus, and the detection assembly may send the detection result to the processing device. After the processing device receives the detection result, the processing device may generate a positioning instruction so that the processing device may acquire a three-dimensional body surface image of the patient, in a case that it is determined that the support apparatus satisfies a specific triggering condition according to the detection result.

Optionally, after the processing device receives the positioning instruction, the processing device may send an image acquisition instruction to the stereo camera. After the stereo camera receives the instruction, the stereo camera starts to collect the three-dimensional body surface image of the patient, and the stereo camera may send the collected three-dimensional body surface image to the processing device. To this end, that the three-dimensional body surface image of the patient by the processing device is acquired may include the three-dimensional body surface image of the patient is acquired by the stereo camera.

In the present disclosure, the stereo camera may face the support apparatus in the radiotherapy device. After the patient is on the support apparatus, the stereo camera may emit structured light to the patient on the support apparatus and receive the structured light reflected by the patient's body surface, so that the stereo camera can collect the three-dimensional body surface image of the patient.

It should be noted that, the coordinate information of each data point or point cloud data in the three-dimensional body surface image of the patient collected by the stereo camera is the coordinate information in the three-dimensional coordinate system of the stereo camera. Therefore, after the stereo camera sends the collected three-dimensional body surface image of the patient to the processing device, the processing device not only needs to receive the three-dimensional body surface image of the patient, but also needs to convert the coordinate system of each data point or point cloud data in the three-dimensional body surface image of the patient into the coordinate information in the three-dimensional coordinate system of the support apparatus, according to the calibration relationship between the three-dimensional coordinate system of the stereo camera and the three-dimensional coordinate system of the support apparatus. In this way, the three-dimensional body surface image of the patient and the first body surface reference image are both in the same coordinate system, and the deviation therebetween may represent the deviation between the patient's pre-positioning and post-positioning.

Optionally, the processing device may also acquire a real-time image of the patient on the support apparatus through the photographing apparatus. In this way, after the processing device acquires the three-dimensional body surface image of the patient, the first body surface reference image of the patient, and the real-time image of the patient, the processing device may overlay at least two of the three-dimensional body surface image of the patient, the first body surface reference image of the patient, and the real-time image of the patient, and send the overlaid image to a display with which the processing device connects and communicates, so that the display can display the overlaid image.

After the processing device overlays the three-dimensional body surface image of the patient and the real-time image of the patient, if the overlaid image is displayed on the display, it is convenient for the operator to observe whether the overlap of body surface between the three-dimensional body surface image of the patient and the real-time image of the patient meets the requirements. If the operator observes that the overlap of body surface between the three-dimensional body surface image of the patient and the real-time image of the patient does not meet the requirements, the operator needs to control the processing device to regenerate the three-dimensional body surface image of the patient.

After the processing device overlays the three-dimensional body surface image of the patient and the first body surface reference image of the patient, if the overlaid image is displayed on the display, it is convenient for the operator to observe whether there is a deviation therebetween, so that the operator may know the current positioning of the patient. In an example, the processing device may process the three-dimensional body surface image of the patient and the first body surface reference image into different colors, and overlay them and send them to the display with which the processing device connects and communicates, so that the display interface of the display shows the three-dimensional body surface image of the patient and the first body surface reference image with different colors, which is convenient for the operator to observe the current positioning of the patient more intuitively.

After the processing device overlays the three-dimensional body surface image of the patient and the real-time image of the patient, if the overlaid image is displayed on the display, the operator may also know the current positioning of the patient.

It should be noted that, after the processing device overlays the three-dimensional body surface image of the patient, the first body surface reference image of the patient and the real-time image of the patient, when the display shows the overlaid image, it may be not only convenient for the operator to observe whether the overlap of body surface between the three-dimensional body surface image of the patient and the real-time image of the patient meets the requirements, but also may allow the operator to know the current positioning of the patient.

In addition, which two or three of the three-dimensional body surface image of the patient, the first body surface reference image of the patient and the real-time image of the patient are overlaid and displayed by the display may be set by the operator as required.

In step 304, the first deviation between the three-dimensional body surface image of the patient and the first body surface reference image in each coordinate direction in the three-dimensional coordinate system of the support apparatus is determined, based on the three-dimensional body surface image of the patient and the first body surface reference image; and the first deviation is output.

In the embodiments of the present disclosure, after the processing device acquires the three-dimensional body surface image of the patient, the processing device may determine the first deviation between the three-dimensional body surface image of the patient and the first body surface reference image in each coordinate direction in the three-dimensional coordinate system of the support apparatus, based on the three-dimensional body surface image of the patient and the first body surface reference image, and output the first deviation. Subsequently, the support apparatus can move according to the first deviation in the various coordinate directions until the first deviation is within a preset threshold range after the movement.

In an example, the first deviation in each coordinate direction may include the translation offset in each coordinate direction; or the first deviation in each coordinate direction may include the translation offset in each coordinate direction and the rotation offset in the corresponding direction. For example, it is assumed that various coordinate directions in the three-dimensional coordinate system of the support apparatus include an X-axis direction (the width direction of the treatment couch), a Y-axis direction (the length direction of the treatment couch) and a Z-axis direction (the height direction of the treatment couch), respectively. Then, the first deviation in various coordinate directions may include a translation offset in the X-axis direction, a translation offset in the Y-axis direction and a translation offset in the Z-axis direction, that is, the first deviation is three-dimensional deviation data. Alternatively, the first deviation in various coordinate directions may include a translation offset and a rotation offset in the X-axis direction, a translation offset and a rotation offset in the Y-axis direction and a translation offset and a rotation offset in the Z-axis direction, that is, the first deviation is six-dimensional deviation data.

It should be noted that, the three-dimensional body surface image of the patient and the first body surface reference image can both refer to the body surface of the same patient. Therefore, in the three-dimensional coordinate system of the support apparatus, there is a corresponding relationship between each data point or point cloud data in the three-dimensional body surface image of the patient and each data point or point cloud data in the first body surface reference image. In this way, the processing device may acquire the first coordinate information of the three-dimensional body surface image of the patient and the second coordinate information of the first body surface reference image within the three-dimensional coordinate system of the support apparatus. The first coordinate information is the coordinate information of each data point or point cloud data in the three-dimensional body surface image of the patient, and the second coordinate information is the coordinate information of each data point or point cloud data in the first body surface reference image.

Afterwards, according to the first coordinate information and the second coordinate information, as well as the corresponding relationship between each data point or point cloud data in the three-dimensional body surface image of the patient and each data point or point cloud data in the first body surface reference image, the processing device may determine the translation offsets in the X-axis direction, the Y-axis direction and the Z-axis direction of the three-dimensional coordinate system of the support apparatus between the three-dimensional body surface image of the patient and the first body surface reference image; or, determine the translation and rotation offsets in the X-axis direction, the Y-axis direction and the Z-axis direction in the three-dimensional coordinate system of the support apparatus.

Figure 5:
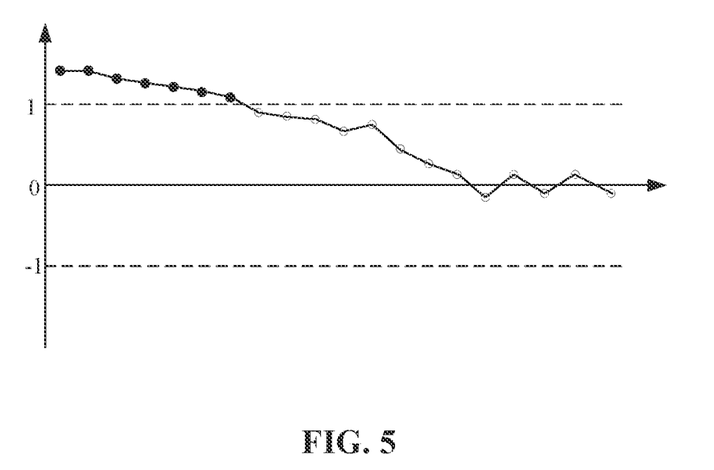
FIG. 5 is an effect diagram of displaying a first deviation on a display according to an embodiment of the present disclosure.

In the present disclosure, after the processing device determines the first deviation in various coordinate directions, the processing device may send the first deviation to the display with which the processing device connects and communicates, so that the display can display the first deviation output by the processing device. In an example, the first deviation may be represented in a two-dimensional coordinate system, the translation offset in the X-axis direction of the first deviation is taken as an example, as shown in FIG. 5, which is an effect diagram of displaying the first deviation on a display according to an embodiment of the present disclosure. In the two-dimensional coordinate system, the abscissa represents time and the unit thereof includes seconds; and the ordinate represents the translation offset in the X-axis direction and the unit thereof includes millimeters. Since the processing device acquires the three-dimensional body surface image of the patient in real time, the processing device may periodically determine the translation offset in the X-axis direction of the first deviation between the three-dimensional body surface image of the patient and the first body surface reference image. For example, the processing device may determine the translation offset in the X-axis direction every 0.1 second. In this way, the distribution of translation offsets in the X-axis direction at different times may be acquired over time. In the two-dimensional coordinate system shown in FIG. 5, after the translation offsets in the X-axis direction at different times in sequence are connected, a curve for representing the change of the translation offsets in the X-axis direction at different times can be obtained. In this way, it is more convenient for the operator to know the magnitude of the translation offsets in the X-axis direction at different times.

It should be noted that, when the first deviation in each coordinate direction includes the translation offset in each coordinate direction, the translation offset in the X-axis direction, the translation offset in the Y-axis direction and the translation offset in the Z-axis direction may be displayed in the same two-dimensional coordinate system or in different two-dimensional coordinate systems. When the first deviation in each coordinate direction includes the translation offset in each coordinate direction and the rotation offset in the corresponding direction, the translation offset in the X-axis direction, the translation offset in the Y-axis direction and the translation offset in the Z-axis direction may be displayed in the same two-dimensional coordinate system, and the rotation offset in the X-axis direction, the rotation offset in the Y-axis direction and the rotation offset in the Z-axis direction may be displayed in the same two-dimensional coordinate system.

In the embodiments of the present disclosure, the support apparatus may be a three-dimensional couch or a six-dimensional couch. When the support apparatus is a three-dimensional couch, the support apparatus can move along each coordinate direction in the three-dimensional coordinate system of the support apparatus, but cannot rotate around each coordinate direction. When the support apparatus is a six-dimensional couch, the support apparatus can move along each coordinate direction in the three-dimensional coordinate system of the support apparatus, and the support apparatus can also rotate around each coordinate direction. Therefore, for different types of support apparatuses, the processing device subsequently processes the determined first deviations in different ways. The embodiments of the present disclosure will take the following two implementations as examples for illustrative description.

In a first implementation, the support apparatus is a three-dimensional couch. When the first deviation in each coordinate direction determined by the processing device includes a translation offset in each coordinate direction, a preset threshold range includes a preset translation offset threshold range. When the first deviation in each coordinate direction determined by the processing device includes a translation offset in each coordinate direction and a rotation offset in the corresponding direction, the preset threshold range includes a preset rotation offset threshold range and a preset translation offset threshold range. Thus, the present disclosure will take the following two cases as examples for illustrative description.

In the first case, the first deviation in each coordinate direction includes the rotation offset in each coordinate direction. After the processing device determines the first deviation, the positioning method according to the embodiments of the present disclosure may further include the following steps.

In step A1, it is detected that whether the rotation offset in each coordinate direction is within a preset rotation offset threshold range.

In the embodiments of the present disclosure, the processing device may detect whether the rotation offset in each coordinate direction is within a preset rotation offset threshold range.

In an example, the preset rotation offset threshold may range from −1 degree to 1 degree.

In step B1, if it is detected that the rotation offset in at least one coordinate direction of the rotation offsets in various coordinate directions is not within the preset rotation offset threshold range, first prompt information is output.

In the embodiments of the present disclosure, if the processing device detects that the rotation offset in at least one coordinate direction of the rotation offsets in various coordinate directions is not within the preset rotation offset threshold range, the processing device may output the first prompt information. The first prompt information is used to prompt the operator to adjust the position of the patient on the support apparatus.

In an example, the first prompt information may include, but is not limited to, text information, picture information, graphic information, or voice information, etc. The processing device may send the first prompt information to the display with which the processing device connects and communicates, so that the first prompt information may be presented on the display interface of the display. In this way, after viewing the first prompt information, the operator may readjust the position of the patient on the support apparatus according to the first prompt information.

After the adjustment of the patient's position is completed, the operator may trigger the positioning instruction again through the first virtual key of "one-key positioning" on the display; or, when the processing device detects through the detection assembly that the patient has moved on the support apparatus and a predetermined delay time has passed, the positioning instruction is automatically generated. That is, the processing device needs to execute the following step C1.

In an example, after the processing device detects that the rotation offset in at least one coordinate direction is not within the preset rotation offset threshold range, the processing device may generate the first prompt information according to the rotation offset in the at least one coordinate direction. In this way, the first prompt information may carry the information of the rotation offset in the at least one coordinate direction. Subsequently, the operator may adjust the position of the patient according to the information of the rotation offset in the at least one coordinate direction carried in the first prompt information. In this way, after the operator adjusts the position of the patient, the rotation offset of the patient may be closer to the preset rotation offset threshold range, effectively improving the efficiency of the operator's adjustment of the position of the patient.

In step C1, if the positioning instruction is received again, the operation of acquiring the three-dimensional body surface image of the patient is re-performed.

In the embodiments of the present disclosure, after the operator completes the adjustment of the patient's position, the operator may trigger the positioning instruction again or the processing device may automatically generate a new positioning instruction. In this way, if the processing device receives the positioning instruction again, the processing device may re-perform the operation of acquiring the three-dimensional body surface image of the patient. That is, the processing device needs to re-perform the above steps 303, 304 and A1 in sequence.

In step D1, if it is detected that the rotation offset in each coordinate direction is within the preset rotation offset threshold range, the translation offset in each coordinate direction is determined as the correction offset.

In the embodiments of the present disclosure, if the processing device detects that the rotation offsets in various coordinate directions are all within the preset rotation offset threshold range, the processing device may determine the translation offset in each coordinate direction as the correction offset (the correction offset here is not within the preset translation offset threshold range). Subsequently, the support apparatus moves only according to the correction offset until the first deviation is within the preset translation offset threshold range after the movement.

It should be noted that when the processing device detects that the rotation offsets in various coordinate directions are all within the preset rotation offset threshold range, the processing device needs to process the translation offset in each coordinate direction. Reference is made to the following second case for details of the processing mode, which are not repeated in the embodiments of the present disclosure.

In the second case, the first deviation in each coordinate direction includes the translation offset in each coordinate direction, or the first deviation in each coordinate direction includes the translation offset in each coordinate direction and the rotation offset in the corresponding direction, and the rotation offsets in various coordinate directions are all within the preset rotation offset threshold range. After the processing device determines the first deviation, the positioning method according to the embodiments of the present disclosure may further include the following steps.

In step A2, it is detected that whether the translation offset in each coordinate direction is within a preset translation offset threshold range.

In the embodiments of the present disclosure, the processing device may detect whether the translation offset in each coordinate direction is within a preset translation offset threshold range, and generate a detection result. The detection result includes whether the translation offset in each coordinate direction is within the preset translation offset threshold range. In an example, the preset translation offset threshold may range from −1 mm to 1 mm.

In step B2, second prompt information is output according to the detection result.

In the embodiments of the present disclosure, the processing device may output the second prompt information according to the detection result. The second prompt information is used to prompt the operator that the translation offset in at least one coordinate direction of the translation offsets in various coordinate directions is outside the second preset range.

In an example, the second prompt information may include, but is not limited to, text information, picture information, graphic information, or voice information, etc. The processing device may send the second prompt information to the display with which the processing device connects and communicates, so that the second prompt information may be presented on the display interface of the display. In this way, after viewing the second prompt information, the operator may control the support apparatus to move according to the second prompt information. For example, a second virtual key for controlling the movement of the support apparatus may be displayed on the display interface of the display. After the operator presses the second virtual key, the processing device may receive an instruction for controlling the movement of the support apparatus triggered by the second virtual key, so that the processing device may control the movement of the support apparatus through the control device. That is, the processing device needs to perform the following step 305.

In the second implementation, when the support apparatus is a six-dimensional couch, the first deviation in each coordinate direction determined by the processing device may include the translation offset in each coordinate direction and the rotation offset in the corresponding direction. After the processing device determines the first deviation, the positioning method according to the embodiments of the present disclosure may further include the following steps.

In step A3, it is detected that whether the rotation offset in each coordinate direction is within the preset rotation offset threshold range and whether the translation offset in each coordinate direction is within the preset translation offset threshold range.

In the embodiments of the present disclosure, the processing device may detect whether the rotation offset in each coordinate direction is within the preset rotation offset threshold range, may detect whether the translation offset in each coordinate direction is within the preset translation offset threshold range and generate test result. The detection result includes: whether the rotation offset in each coordinate direction is within the preset rotation offset threshold range and whether the translation offset in each coordinate direction is within the preset translation offset threshold range.

In step B3, the third prompt information is output according to the detection result.

In the embodiments of the present disclosure, the processing device may output the third prompt information according to the detection result. The third prompt information is used to prompt the operator that the rotation offset in at least one coordinate direction of the rotation offsets in various coordinate directions is outside the preset rotation offset threshold range, and/or, the translation offset in at least one coordinate direction of the translation offsets in various coordinate directions is outside the preset translation offset threshold range.

In an example, the third prompt information may include, but is not limited to, text information, picture information, graphic information, or voice information, etc. The processing device may send the third prompt information to the display with which the processing device connects and communicates, so that the third prompt information may be presented on the display interface of the display. In this way, after viewing the third prompt information, the operator may control the support apparatus to move according to the third prompt information. For example, a second virtual key may be displayed on the display interface of the display. After the operator presses the second virtual key, the processing device may receive an instruction for controlling the movement of the support apparatus triggered by the second virtual key, so that the processing device may control the movement of the support apparatus through the control device. That is, the processing device needs to perform the following step 305.

It should be noted that, when the display displays the first deviation in each coordinate direction, the display may differently display first deviations at different times. For example, as shown in FIG. 5, for the translation offset in the X-axis direction in the first deviation, when the translation offset in the X-axis direction at a certain moment is outside the preset translation offset threshold range, the translation offset in the X-axis direction at that moment may be represented by a black dot; and when the translation offset in the X-axis direction is within the preset translation offset threshold range at a certain moment, the translation offset in the X-axis direction at that moment may be represented by a white dot. In this way, the operator can view more intuitively at which moments the first deviation is within the preset threshold range and at which moments the first deviation is outside the preset threshold range.

It should also be noted that, after the processing device outputs the first deviation in various coordinate directions, the processing device may determine the first deviation in various coordinate directions between the three-dimensional body surface image of the patient and the first body surface reference image again, so as to improve the accuracy of the first deviation determined by the processing device. In this case, if the processing device receives the positioning instruction again, the processing device may re-perform the operation of acquiring the three-dimensional body surface image of the patient. That is, the processing device needs to re-perform the above steps 303 and 304 in sequence.

In step 305, the first deviation in each coordinate direction is sent to the control device, so that the control device can control the support apparatus to move based on the first deviation in each direction until the first deviation is within a preset threshold range after the movement.

In the embodiments of the present disclosure, after the processing device receives the instruction for controlling the movement of the support apparatus, the processing device may send the first deviation in each coordinate direction to the control device. In this way, after the control device receives the first deviation in each coordinate direction, it can control the support apparatus to move based on the first deviation in each coordinate direction until the first deviation is within the preset threshold range after the movement, and thus the positioning of the patient is completed.

The first body surface reference image may include the body surface image of the patient when the target point of the patient coincides with the isocenter of the radiotherapy device. Therefore, after the first deviation between the three-dimensional body surface image of the patient and the first body surface reference image in each coordinate direction in the three-dimensional coordinate system of the support apparatus is within the preset threshold range, the three-dimensional body surface image of the patient and the first body surface reference image are substantially coincident, and the target point of the patient on the support apparatus may be coincident with the isocenter of the radiotherapy device.

It should be noted that, in the process of controlling the movement of the support apparatus by the control device, the processing device needs to acquire the three-dimensional body surface image of the patient on the support apparatus through the stereo camera in real time. In this way, when the support apparatus moves so that the patient thereon moves, the three-dimensional body surface image of the patient acquired by the processing device also moves therewith. In the three-dimensional coordinate system of the support apparatus, the three-dimensional body surface image of the patient moves until it substantially coincides with the first body surface reference image and the control device may stop controlling the movement of the support apparatus, and thus the process of positioning the patient may be completed.

In the embodiments of the present disclosure, since the support apparatus may be a three-dimensional couch or a six-dimensional couch, the movement modes of different types of support apparatuses are also different. Therefore, the embodiments of the present disclosure will be described by taking the following two optional implementations as examples.

In the first optional implementation, the support apparatus is a three-dimensional couch. The processing device only needs to send the translation offsets in various coordinate directions to the control device. After receiving the translation offsets in various coordinate directions, the control device may detect whether the translation offsets in various coordinate directions are within the preset translation offset threshold range. If the translation offset in a certain coordinate direction is not within the preset translation offset threshold range, the control device may determine the coordinate direction as the first target direction and subsequently control the support apparatus to move by a target translation offset in a direction corresponding to the first target direction. The target translation offset includes the translation offset in the first target direction.

In an example, the first target direction may include one coordinate direction, or may include a plurality of coordinate directions. When the first target direction includes a plurality of coordinate directions, the control device needs to control the support apparatus to move in a plurality of directions corresponding to the plurality of coordinate directions. For example, assuming that the translation offsets in various coordinate directions are all outside the preset translation offset threshold range, the control device may determine the various coordinate directions as the first target direction. In this case, the control device may firstly control the support apparatus to move by a first target translation offset along a direction corresponding to the X-axis direction; then control the support apparatus to move by a second target translation offset along a direction corresponding to the Y-axis direction; and finally control the support apparatus to move by a third target translation offset along a direction corresponding to the Z-axis direction. The first target translation offset is the translation offset in the X-axis direction, the second target translation offset is the translation offset in the Y-axis direction and the third target translation offset is the translation offset in the Z-axis direction.

In the second optional implementation, the support apparatus is a six-dimensional couch. The processing device not only needs to send the translation offsets in various coordinate directions to the control device, but also needs to send the rotation offsets in various coordinate directions to the control device. Reference may be made to the first optional implementation described above for the mode in which the control device controls the movement of the support apparatus based on the translation offsets in various coordinate directions, which will not be repeated in the embodiments of the present disclosure.

For the mode in which the control device controls the rotation of the support apparatus based on the rotation offsets in various coordinate directions, the control device may detect whether the rotation offsets in various coordinate directions are within the preset rotation offset threshold range. If the rotation offset in a certain coordinate direction is not within the preset rotation offset threshold range, the control device may determine the coordinate direction as the second target direction and subsequently control the support apparatus to rotate by a target rotation offset around a direction corresponding to the second target direction. The target rotation offset includes the rotation offset in the second target direction.

In an example, the second target direction may include one coordinate direction, or may include a plurality of coordinate directions. When the second target direction includes a plurality of coordinate directions, the control device needs to control the support apparatus to rotate around a plurality of directions corresponding to the plurality of coordinate directions. For example, assuming that the rotation offsets in various coordinate directions are all outside the preset rotation offset threshold range, the control device may determine the various coordinate directions as a second target direction. In this case, the control device may firstly control the support apparatus to rotate by a second target rotation offset around a direction corresponding to the X-axis direction; then control the support apparatus to rotate by a second target rotation offset around a direction corresponding to the Y-axis direction; and finally control the support apparatus to rotate by a third target rotation offset around a direction corresponding to the Z-axis direction. The first target rotation offset is the rotation offset in the X-axis direction, the second target rotation offset is the rotation offset in the Y-axis direction and the third target rotation offset is the rotation offset in the Z-axis direction.

It should be noted that, after the first deviation in various coordinate directions is within the preset threshold range, the server may determine that the positioning of the patient has been completed, and the processing device may output fourth prompt information. The fourth prompt information is used to prompt the operator that the positioning of the patient has been completed. For example, the fourth prompt information may include, but is not limited to, text information or voice information or the like. The processing device may send the fourth prompt information to the display with which the processing device connects and communicates, so that the fourth prompt information may be presented on the display interface of the display. In this way, after viewing the fourth prompt information, the operator may know that the positioning of the patient has been completed according to the fourth prompt information, so that the operator may control the radiotherapy device to treat the patient. Subsequently, the server needs to perform the following step 306.

It should also be noted that, if the radiotherapy device performs radiotherapy on the patient for many times, the patient needs to be positioned before each radiotherapy is performed on the patient. When the patient is positioned for the first time, the first body surface reference image may be generated by a plurality of medical pictures of the patient stored in the TPS server; and when the patient is positioned subsequently, the body surface image of the patient after the first positioning may be used as the first body surface reference image.

In step 306, a three-dimensional body surface image of the patient on the support apparatus is acquired, after an instruction for monitoring the movement of the patient during treatment is received.

In the embodiments of the present disclosure, after the instruction for monitoring the movement of the patient during treatment is received, the processing device needs to continue acquiring the three-dimensional body surface image of the patient on the support apparatus.

In an example, a display interface of a display which connects and communicates with the processing device may display a third virtual key for monitoring the movement of the patient during treatment. After the operator views the fourth prompt information and knows that the current positioning of the patient has been completed, the operator may press the third virtual key on the display interface of the display, so that the processing device may receive the instruction triggered by the third virtual key for monitoring the movement of the patient during treatment, and thus the processing device may continue to acquire the three-dimensional body surface image of the patient. It should be noted that, reference may be made to the relevant content in step 303 in the embodiments described above for the mode in which the processing device acquires the three-dimensional body surface image of the patient, which will not be repeated in the embodiments of the present disclosure. It also should be noted that, the instruction for monitoring the movement of the patient during treatment may be automatically generated by the processing device after outputting the fourth prompt information.

In step 307, a second deviation between the three-dimensional body surface image of the patient and the second body surface reference image in each coordinate direction in the three-dimensional coordinate system of the support apparatus is determined based on the three-dimensional body surface image of the patient and the second body surface reference image, so as to detect the movement of the patient.

In the embodiments of the present disclosure, after the processing device acquires the three-dimensional body surface image of the patient, the processing device may determine the second deviation between the three-dimensional body surface image of the patient and the second body surface image in each coordinate direction in the three-dimensional coordinate system of the support apparatus based on the three-dimensional body surface image of the patient and the second body surface reference image, so as to detect the movement of the patient.

Optionally, after the processing device acquires the second deviation in each coordinate direction, the processing device may further output the second deviation. It should be noted that the content included in the second deviation is the same as the content included in the first deviation in the foregoing embodiments. Therefore, reference may be made to the content in the foregoing step 304 for the mode in which the processing device outputs the second deviation and the mode in which the processing device subsequently processes the second deviation, which will not be repeated in the embodiments of the present disclosure.

It should also be noted that when the processing device determines that the second deviation in various directions is not within the preset threshold range, the support apparatus needs to move according to the second deviation. Reference may be made to the content in step 305 in the foregoing embodiments for the mode in which the support apparatus moves according to the second deviation, which will not be repeated in the embodiments of the present disclosure.

In the embodiments of the present disclosure, there are various modes for the processing device to acquire the second body surface reference image. In a first exemplary implementation, the processing device may use the first body surface reference image as the second body surface reference image. In a second exemplary implementation, the processing device may use the three-dimensional image of the body surface of the patient on the support apparatus as the second body surface reference image after the first deviation in each coordinate direction is within the preset threshold range image.

For the second exemplary implementation described above, the modes of acquiring the second body surface reference image by the processing device are also different for different types of radiotherapy devices. In a case that the radiotherapy device is a C-arm type radiotherapy device. Since the C-arm type radiotherapy device has only one isocenter, after the positioning of the patient is completed, the support apparatus does not need to be moved and the radiotherapy device can directly treat the patient. Therefore, when the second deviation in various coordinate directions is within the preset threshold range, the processing device may directly determine the current three-dimensional body surface image of the patient as the second body surface reference image.

In another case, the radiotherapy device is a roller type radiotherapy device. Since the roller type radiotherapy device has two isocenters, after the positioning of the patient is completed, the support apparatus needs to move by a preset distance before the radiotherapy device can treat the patient. Therefore, after the first deviations in various coordinate directions are within the preset threshold range, and when the support apparatus moves by a preset distance, the processing device may determine the current three-dimensional body surface image of the patient as the second body surface reference image.

Optionally, after the processing device acquires the three-dimensional body surface image of the patient, the second body surface reference image of the patient, and the real-time image of the patient, the processing device may overlay at least two of the three-dimensional body surface image of the patient, the second body surface reference image of the patient and the real-time image of the patient, and send the overlaid image to a display with which the processing device connects and communicates, so that the display can display the overlaid processed image.

It should be noted that the sequence of steps of the positioning method according to the embodiments of the present disclosure may be appropriately adjusted, and the steps may also be correspondingly increased or decreased according to situations. Any skilled person who is familiar with the technical field may easily conceive of the changed methods within the technical scope disclosed in the present disclosure, which should be covered within the protection scope of the present disclosure, and are not repeated here.

In summary, in the positioning method according to the embodiments of the present disclosure, the body surface image of the patient is acquired, and based on the three-dimensional body surface image of the patient and the first body surface reference image, the first deviation therebetween is determined, so that the support apparatus can move according to the first deviation. After the first deviation is within the preset threshold range, the target point of the patient on the patient support apparatus coincides with the isocenter of the radiotherapy device, and the positioning of the patient is completed. In this way, the positioning of the patient can be achieved without using a laser light, and in the process of positioning the patient through the three-dimensional body surface image of the patient and the first body surface reference image, each data point or point cloud data of the three-dimensional body surface image of the patient may act as a marker for the patient body surface setting, which effectively improves the accuracy of positioning the patient, thereby improving the effect of subsequent treatment of the patient with the radiotherapy device.

Figure 6:
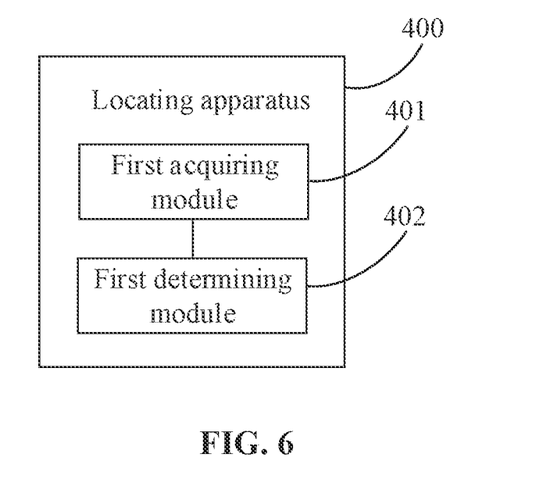
FIG. 6 is a structural block diagram of a positioning apparatus according to an embodiment of the present disclosure.

Reference is made to FIG. 6, which is a structural block diagram of a positioning apparatus according to an embodiment of the present disclosure. The positioning apparatus 400 may be integrated into the processing device 101 in the radiotherapy system 100 shown in FIG. 1 or FIG. 2. The positioning apparatus 400 may include:
  a first acquiring module 401 configured to acquire a three-dimensional body surface image of the patient on the support apparatus after receiving a positioning instruction; and
  a first determining module 402 configured to determine, based on the three-dimensional body surface image of the patient and the first body surface reference image, a first deviation between the three-dimensional body surface image of the patient and the first body surface reference image in each coordinate direction in the three-dimensional coordinate system, so that the support apparatus can move according to the first deviation in each coordinate direction until the first deviation is within the preset threshold range after the movement.

The first body surface reference image is a three-dimensional contour image of the patient's body surface when the target point of the patient coincides with the isocenter of the radiotherapy device.

In summary, by the positioning apparatus according to the embodiments of the present disclosure, the body surface image of the patient is acquired, and based on the three-dimensional body surface image of the patient and the first body surface reference image, the first deviation therebetween is determined, so that the support apparatus can move according to the first deviation. After the first deviation is within the preset threshold range, the target point of the patient on the patient support apparatus coincides with the isocenter of the radiotherapy device, and the positioning of the patient is completed. In this way, as long as the positioning instruction is received, the patient may be positioned automatically through the body surface image. The patient can be positioned without manual adjustment by the operator, which completely replaces the laser light and improves the accuracy and efficiency of positioning the patient.

Optionally, the first deviation in each coordinate direction includes the translation offset in each coordinate direction. Correspondingly, the preset threshold range includes a preset translation offset threshold range. Alternatively, the first deviation in each coordinate direction includes the translation offset in each coordinate direction and the rotation offset in the corresponding direction. Correspondingly, the preset threshold range includes a preset rotation offset threshold range and a preset translation offset threshold range.

Optionally, the first deviation in each coordinate direction includes a rotation deviation in each coordinate direction. In the case that the support apparatus is a three-dimensional couch, the positioning apparatus may also include:
  a first detection module configured to detect whether the rotation offset in each coordinate direction is within the preset rotation offset threshold range; and
  a first prompting module configured to output first prompt information upon detecting that the rotation offset in at least one coordinate direction of the rotation offsets in various coordinate directions is not within the preset rotation offset threshold range, and the first prompt information is used to prompt the operator to adjust the position of the patient on the support apparatus.

Optionally, the positioning apparatus may further include a correction offset determining module configured to determine the translation offset in each coordinate direction as the correction offset upon detecting that the rotation offsets in various coordinate directions are all within the preset rotation offset threshold range, so that the support apparatus can move according to the correction offset, until the first deviation is within the preset translation offset threshold range after the movement.

Optionally, the first acquiring module 401 is further configured to re-perform the operation of acquiring the three-dimensional body surface image of the patient if the positioning instruction is received again.

Optionally, the first deviation in each coordinate direction includes the translation offset in each coordinate direction; or, the first deviation in each coordinate direction includes the translation offset in each coordinate direction and the rotation offset in the corresponding direction. When the rotation offset in each coordinate direction is within the preset rotation offset threshold range, the positioning apparatus may also include:
  a second detection module configured to detect whether the translation offset in each coordinate direction is within the preset translation offset threshold range; and
  a second prompting module configured to output second prompting information according to the detection result, and the second prompting information is used to prompt the operator that the translation offset in at least one coordinate direction of the translation offsets in various coordinate directions is outside the preset translation offset threshold range.

Figure 7:
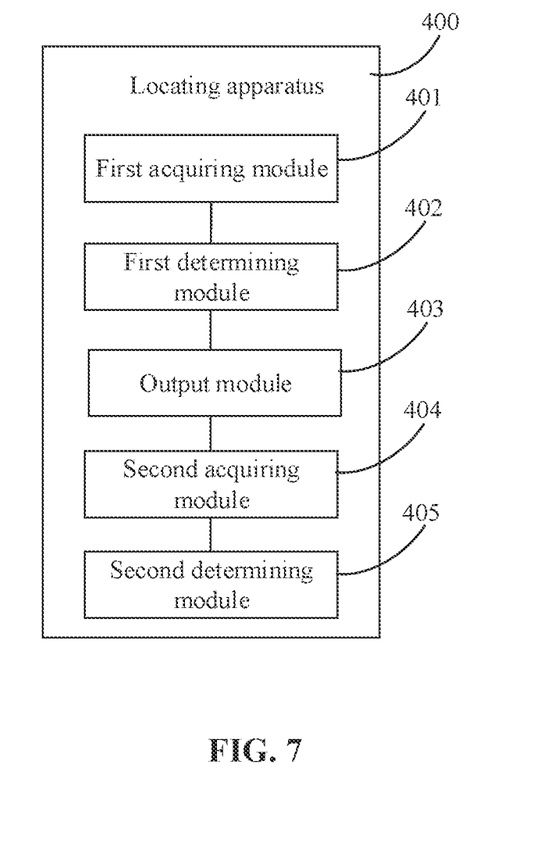
FIG. 7 is a structural block diagram of another positioning apparatus according to an embodiment of the present disclosure.

Optionally, as shown in FIG. 7, FIG. 7 is a structural block diagram of another positioning apparatus according to an embodiment of the present disclosure. The positioning apparatus 400 may further include an output module 403 for outputting the first deviation in each coordinate direction.

Optionally, as shown in FIG. 7, the positioning apparatus 400 may further include:
- a second acquiring module 404 configured to acquire a three-dimensional body surface image of the patient on the support apparatus after receiving the instruction for monitoring the movement of the patient during treatment; and
- a second determining module 405 configured to determine, based on the three-dimensional body surface image of the patient and the second body surface reference image, the second deviation between the three-dimensional body surface image of the patient and the second body surface reference image in each coordinate direction, to monitor the movement of the patient.

Optionally, the first acquiring module 401 or the second acquiring module 404 is configured to acquire a three-dimensional body surface image of the patient through a stereo camera.

In summary, by the positioning apparatus according to the embodiments of the present disclosure, the body surface image of the patient is acquired, and based on the three-dimensional body surface image of the patient and the first body surface reference image, the first deviation therebetween is determined, so that the support apparatus can move according to the first deviation. After the first deviation is within the preset threshold range, the target point of the patient on the patient support apparatus coincides with the isocenter of the radiotherapy device, and the positioning of the patient is completed. In this way, the positioning of the patient can be achieved without using a laser light. After receiving the positioning instruction, the positioning of the patient can be achieved through the three-dimensional body surface image of the patient and the first body surface reference image, which improves the accuracy and efficiency of positioning the patient. During the positioning, each data point or point cloud data in the three-dimensional body surface image of the patient may be used as a marker for the patient body surface setting, which effectively improves the accuracy of positioning the patient, thereby improving the effect of treating the patient with the radiotherapy device subsequently.

Those skilled in the art may clearly understand that, for the convenience and brevity of description, for the specific working processes of the above-described apparatuses and modules, reference may be made to the corresponding processes in the foregoing method embodiments, which will not be repeated here.

In practical applications, each module and each unit of the module in this embodiment may be implemented by a central processing unit (CPU), a microprocessor (MPU), a digital signal processor (DSP) or a field programmable gate array (FPGA) or a modulator-demodulator or other devices on the positioning apparatus.

An embodiment of the present disclosure further provides a processing device, and the processing device may be the processing device 101 in the radiotherapy system 100 shown in FIG. 1 or FIG. 2. The positioning apparatus 400 shown in FIG. 6 or FIG. 7 may be integrated in the processing device 101.

The processing device may include a processor, and a memory for storing executable instructions of the processor. The processor is configured to execute the positioning method shown in FIG. 3 or FIG. 4.

An embodiment of the present disclosure also provides a computer-readable storage medium. The computer-readable storage medium stores instructions thereon, when the computer-readable storage medium runs on a processing assembly, the processing assembly executes the positioning method shown in FIG. 3 or FIG. 4.

In the present disclosure, the terms "first" and "second" are used for descriptive purposes only, and should not be construed to indicate or imply relative importance. The term "a plurality of" refers to two or more, unless expressly limited otherwise.

Those of ordinary skill in the art can understand that all or part of the steps of implementing the above embodiments may be completed by hardware, or may be completed by instructing relevant hardware through a program, and the program may be stored in a computer-readable storage medium. The storage medium described above may be a read-only memory, a magnetic disk or an optical disk, etc.

Described above are merely optional embodiments of the present disclosure, but are not intended to limit the present disclosure. Any modifications, equivalent replacements, improvements and the like made within the spirit and principles of the present disclosure should be included within the scope of protection of the present disclosure.

What is claimed is:

1. A positioning method, comprising:
   - acquiring a three-dimensional body surface image of a patient on a support apparatus after receiving a positioning instruction;
   - determining a first deviation between the three-dimensional body surface image of the patient and a first body surface reference image in each coordinate direction in a three-dimensional coordinate system, based on the three-dimensional body surface image of the patient and the first body surface reference image, so that the support apparatus is movable according to the first deviation in each coordinate direction, until the first deviation is within a preset threshold range after movement.

2. The method according to claim 1, wherein the first deviation in each coordinate direction comprises a translation offset in each coordinate direction, and the preset threshold range comprises a preset translation offset threshold range.

3. The method according to claim 2, wherein the first deviation in each coordinate direction further comprises a rotation offset in each coordinate direction, and the preset threshold range further comprises a preset rotation offset threshold range.

4. The method according to claim 3, wherein in a case that the support apparatus is a three-dimensional couch, the method further comprises:
   - detecting whether the rotation offset in each coordinate direction is within the preset rotation offset threshold range; and
   - outputting first prompt information in response to detecting that the rotation offset in at least one coordinate direction of rotation offsets in various coordinate directions is not within the preset rotation offset threshold range, wherein the first prompt information is used to prompt an operator to adjust a position of the patient on the support apparatus.

5. The method according to claim 4, further comprising:
   - determining the translation offset in each coordinate direction as a correction offset in response to detecting that the rotation offsets in various coordinate directions are all within the preset rotation offset threshold range, so that the support apparatus is movable according to the correction offset until the first deviation is within the preset translation offset threshold range after movement.

6. The method according to claim 2, further comprising:
detecting whether the translation offset in each coordinate direction is within the preset translation offset threshold range; and
outputting second prompt information according to a detection result, wherein the second prompt information is used to prompt an operator that the translation offset in at least one coordinate direction of translation offsets in various coordinate directions is outside the preset translation offset threshold range.

7. The method according to claim 1, further comprising:
re-performing an operation of acquiring the three-dimensional body surface image of the patient in response to receiving the positioning instruction again.

8. The method according to claim 1, further comprising:
outputting a first deviation in various coordinate directions.

9. The method according to claim 1, further comprising:
acquiring another three-dimensional body surface image of the patient on the support apparatus after receiving an instruction for monitoring a movement of the patient during treatment; and
determining a second deviation between the three-dimensional body surface image of the patient and a second body surface reference image in each coordinate direction, based on the three-dimensional body surface image of the patient and the second body surface reference image to monitor movement of the patient.

10. The method according to claim 9, wherein the second body surface reference image is a three-dimensional image of the body surface of the patient on the support apparatus after a first deviation in various coordinate directions is within a preset threshold range.

11. The method according to claim 9, wherein the second body surface reference image is the first body surface reference image.

12. The method according to claim 1, wherein acquiring the three-dimensional body surface image of the patient comprises:
acquiring the three-dimensional body surface image of the patient by a stereo camera.

13. The method according to claim 1, further comprising:
overlaying at least two of the three-dimensional body surface image of the patient, the first body surface reference image and a real-time image of the patient.

14. The method according to claim 1, further comprising:
acquiring a plurality of medical pictures of the patient; and
generating the first body surface reference image based on outer contours of the patient in the plurality of medical pictures.

15. A processing device, comprising a processor and a memory for storing executable instructions of the processor, wherein the processor is configured to execute the positioning method according to claim 1.

16. A radiotherapy system, comprising a processing device and a radiotherapy device, wherein the radiotherapy device comprises a support apparatus, and the processing device is the processing device according to claim 15.

17. The radiotherapy system according to claim 16, further comprising a trigger apparatus which connects and communicates with the processing device, wherein the trigger apparatus is configured for sending a positioning instruction to the processing device.

18. The radiotherapy system according to claim 16, further comprising a display which connects and communicates with the processing device, wherein the display is configured for displaying an overlaid image of the at least two of the three-dimensional body surface image of the patient, the first body surface reference image and a real-time image of the patient.

19. The radiation therapy system according to claim 16, further comprising a photographing apparatus which connects and communicates with the processing device, wherein the photographing apparatus is configured to capture a real-time image of the patient.

20. A non-transitory computer-readable storage medium, wherein the non-transitory computer-readable storage medium stores instructions thereon, when the non-transitory computer-readable readable storage medium is executed on a processing assembly, the processing assembly performs the positioning method according to claim 1.

* * * * *